United States Patent
Bhattacharya

(10) Patent No.: US 9,504,431 B2
(45) Date of Patent: Nov. 29, 2016

(54) METHOD AND APPARATUS FOR SENSITIVITY CALIBRATION

(71) Applicant: Siemens Medical Solutions USA, Inc., Malvern, PA (US)

(72) Inventor: Manojeet Bhattacharya, Chicago, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 301 days.

(21) Appl. No.: 14/297,709

(22) Filed: Jun. 6, 2014

(65) Prior Publication Data

US 2014/0371580 A1 Dec. 18, 2014

Related U.S. Application Data

(60) Provisional application No. 61/834,626, filed on Jun. 13, 2013.

(51) Int. Cl.
*A61B 6/03* (2006.01)
*G01T 1/164* (2006.01)
*G01T 7/00* (2006.01)
*A61B 6/00* (2006.01)

(52) U.S. Cl.
CPC .............. *A61B 6/037* (2013.01); *A61B 6/4258* (2013.01); *A61B 6/582* (2013.01); *G01T 1/1647* (2013.01); *G01T 7/005* (2013.01)

(58) Field of Classification Search
CPC .... A61B 6/037; A61B 6/4258; A61B 6/582; G01T 1/1647; G01T 7/005
See application file for complete search history.

(56) References Cited

PUBLICATIONS

Sayed, M., "Quality Control in Nuclear Medicine II. Planar and Single Photon Emission Computed Tomographic Gamma Camera Systems," Turkish Journal of Nuclear Medicine 6(3): 185-189.
"The Selection, Use, Calibration, and Quality Assurance of Radionuclide Calibrators Used in Nuclear Medicine," Report of AAPM Task Group 181, ISBN 978-1-936366-18-7, Jun. 2012, 46 pages.

*Primary Examiner* — Peter Luong

(57) ABSTRACT

A detector of a gamma camera is configured such that a radioactive point source is positioned within a field of view at a fixed distance from the detector. A predetermined number of gamma photons emitted by the point source and passed through a collimator are acquired. A system-specific planar sensitivity is computed for a combination of the collimator and detector using the number of gamma photons acquired, a time duration of the acquisition, and precalibrated radioactivity data of the point source corrected for decay that occurred after a precalibration time. A deviation of the computed system-specific planar sensitivity from a class standard sensitivity value for a combination of the radioactive point source, the collimator, and the detector is computed. A class standard sensitivity value for a combination of a radiopharmaceutical, the collimator, and the detector is scaled by the computed deviation, yielding a scaled system-specific sensitivity value for the radiopharmaceutical.

15 Claims, 8 Drawing Sheets ately to the radioactivity distribution, and the traditional image is only visually interpretable by the physician because it does not contain reliable absolute quantitative information (i.e., information with

METHOD AND APPARATUS FOR SENSITIVITY CALIBRATION

CROSS-REFERENCE TO RELATED APPLICATION

This application claims priority under 35 U.S.C. §119(e) from co-pending U.S. Provisional Application Ser. No. 61/834,626 filed Jun. 13, 2013, the entirety of which is hereby incorporated by reference herein.

FIELD

Aspects of the present disclosure relate in general to medical imaging, and more particularly to calibration techniques for gamma ray based medical imaging.

BACKGROUND

Nuclear medical imaging is a useful technique that is applied in a variety of diagnostic contexts and medical specialties. In one type of nuclear medical imaging known as Single Photon Emission Computed Tomography (SPECT), the primary imaging task is to accurately determine and depict the spatial distribution of a radioactive isotope (radioisotope) used as a tracer (radiotracer) in the imaged object. A radiotracer may also be referred to as a radiopharmaceutical, as it is a pharmaceutical labeled with a radioactive isotope. For example, a patient may be injected with a radioactive pharmaceutical tracer (radiopharmaceutical or radiotracer) containing a radioisotope such as Technetium-99m (Tc-99m). Typically, the tracer travels to a target within the patient's body, and an attached radioactive atom emits gamma ray photons as it undergoes nuclear decay. A gamma camera (also known as an Anger camera or scintillation camera) has one or more detectors located near the patient for detecting emitted gamma rays that have traveled through a portion of the patient's body. The detector(s) are typically flat crystal plane(s) (e.g., 40 cm×50 cm crystals of NaI) that absorb counts of gamma ray photons. The absorbed gamma ray photons cause the crystal of the detector to scintillate, as an electron is dislodged from an atom (e.g., iodine atom) of the crystal and a pulse of light is produced in accordance with the Photoelectric effect and/or Compton effect. The light is detected, e.g., by an array of photomultiplier tubes (PMT) of the gamma camera. A collimator is typically mounted in front of the detector for limiting gamma ray detection to those photons emanating from the acceptance angle of collimator holes in a given field of view.

For SPECT imaging, gamma camera data are acquired from various view angles or projections and reconstructed in various planes in accordance with the principles of three-dimensional (3D) tomography. A gamma camera used for SPECT is also referred to as a SPECT camera. Gamma cameras for SPECT are described in more detail in Sayed, M., "Quality Control in Nuclear Medicine II. Planar and Single Photon Emission Computed Tomographic Gamma Camera Systems," Turkish Journal of Nuclear Medicine 6(3): 185-189 (1997), the entire contents of which are hereby incorporated by reference herein.

Traditionally, the radiotracer distribution has been depicted in units of "proportional counts-per-second (prop-CPS)," i.e., units that are proportional to the radioactivity distribution, and the traditional image is only visually interpretable by the physician because it does not contain reliable absolute quantitative information (i.e., information with reliable units that have a physical basis with its associated measurement uncertainty). In other words, traditional SPECT images depict relative variations in activity concentrations to the trained human observer (e.g., using varying colors or shades of gray) but do not convey absolute quantitative information (i.e., the exact value at a particular voxel does not have a quantifiable physical meaning) Although it is possible to perform semi-quantitative assessment of traditional SPECT images by evaluating lesion-to-background ratios or by comparing the images to databases of normal patient scans, absolute quantification of tracer uptake and in turn disease diagnosis and monitoring has not been possible using traditional methods. An added uncertainty in quantifying the images lies in the fact that until now there has been no method to standardize the performance of SPECT cameras in the field. In other words, there has not been a common baseline across the field for SPECT image acquisition.

SUMMARY

In some embodiments of the present disclosure, a method of normalizing a sensitivity of a gamma camera includes configuring a detector of a gamma camera such that a radioactive point source is positioned within a field of view of the detector at a fixed distance from the detector. The method includes performing a planar acquisition of gamma photons emitted by the radioactive point source and passed through a collimator, until a predetermined number of photons have been acquired. In a planar acquisition of gamma photons, projection data are acquired for a single view angle, as opposed to tomographic acquisition wherein projection data are acquired at multiple angles. A system-specific planar sensitivity is computed for a combination of the collimator and detector using the number of gamma photons acquired, a time duration of the acquisition, and precalibrated radioactivity data of the radioactive point source corrected for decay that occurred after a precalibration time. The method includes computing a deviation of the computed system-specific planar sensitivity from a class standard sensitivity value for a combination of the radioactive point source, the collimator, and the detector. A class standard sensitivity value for a combination of a radiopharmaceutical, the collimator, and the detector is scaled by the computed deviation, to yield a scaled system-specific sensitivity value for the radiopharmaceutical.

In some embodiments, a method of identifying a miscalibrated dose calibrator includes affixing a calibration radioactive source relative to a source holder. The source holder is positioned in a dose calibrator, and radioactivity of the source is measured using the dose calibrator. The method includes computing a deviation of the measured radioactivity from a precalibrated radioactivity value that has been corrected for decay that has occurred since the precalibration time. Responsive to a determination that the computed deviation is outside a range specified by a predetermined threshold, an indication that the dose calibrator is miscalibrated is displayed.

In some embodiments, a radioactive source includes a radioactive isotope encapsulated in an enclosure, a handle portion having an axis aligned with the enclosure, and a substantially conical transition portion connecting the enclosure and the handle portion. The transition portion is aligned along the axis. An angle defined between the axis and a surface of the transition portion is configured to minimize a number of Compton-scattered gamma photons emitted by the isotope that are collimated by a collimator and detected by a detector of a gamma camera.

In some embodiments, a device includes a radioactive point source, a collimator, a gamma ray detector configured to detect gamma photons emitted by the radioactive point source and passed through the collimator, one or more computer processors, and a non-transitory computer readable medium having instructions embodied tangibly thereupon. When executed, the instructions are configured to cause the one or more processors to perform operations of normalizing a sensitivity of a gamma camera. The operations include computing a system-specific planar sensitivity for a combination of the collimator and detector using a number of gamma photons acquired, a time duration of acquisition of the number of gamma photons, and precalibrated radioactivity data of the radioactive point source corrected for decay that occurred after a precalibration time; computing a deviation of the computed system-specific planar sensitivity from a class standard sensitivity value for a combination of the radioactive point source, the collimator, and the detector; and scaling a class standard sensitivity value for a combination of a radiopharmaceutical, the collimator, and the detector by the computed deviation, to yield a scaled system-specific sensitivity value for the radiopharmaceutical.

BRIEF DESCRIPTION OF THE DRAWINGS

The following will be apparent from elements of the figures, which are provided for illustrative purposes and are not necessarily to scale.

DETAILED DESCRIPTION

This description of the exemplary embodiments is intended to be read in connection with the accompanying drawings, which are to be considered part of the entire written description.

Various embodiments of the present disclosure enable improved single photon emission computed tomography (SPECT) imaging that includes reliable absolute radioactivity concentration data. Quantitative SPECT images that provide absolute data as opposed to merely relative data make it possible for SPECT images to be automatically analyzed in new ways. In addition, some embodiments include calibration of system sensitivity to reduce error sources and provide increased confidence in imaging results.

Figure 1:
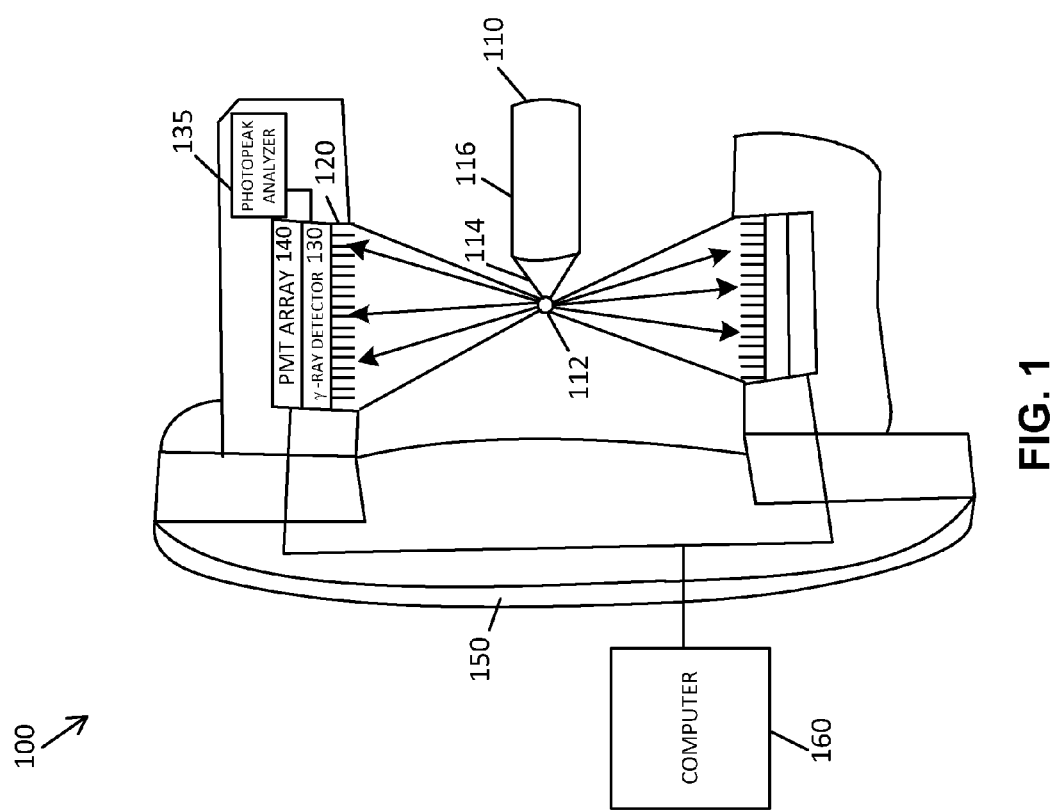
FIG. 1 is a diagram of an imaging device in accordance with some embodiments of the present disclosure.

FIG. 1 is a diagram of an imaging device in accordance with some embodiments of the present disclosure. Device 100 includes a gamma camera having a collimator 120, a gamma ray detector (e.g., planar crystal) 130, a photopeak energy analyzer 135, and a photomultiplier tube array 140. Collimator 120, which may be a low energy high resolution or LEHR collimator, may include a slab (e.g., of lead) defining multiple holes (e.g., hexagonal orifices) separated by septa (not shown). The gamma camera is coupled to a computer 160 that is described in detail farther below. In the example of FIG. 1, a dual-head detector coupled to a gantry 150 is shown, but in some embodiments a single detector or more than two detectors may be used. Device 100 is capable of performing SPECT imaging based on gamma photons emitted by a radiotracer within a patient (not shown) or emitted by radioactive source 110. Radioactive source 110 may be used for calibration and may be referred to as a calibration source. The calibration source includes a radioisotope enclosed within enclosure 112, a transition portion 114, and a handle portion 116. The radioisotope within enclosure 112 acts like a radioactive point source and may be referred to as a calibration point source.

Figure 2:
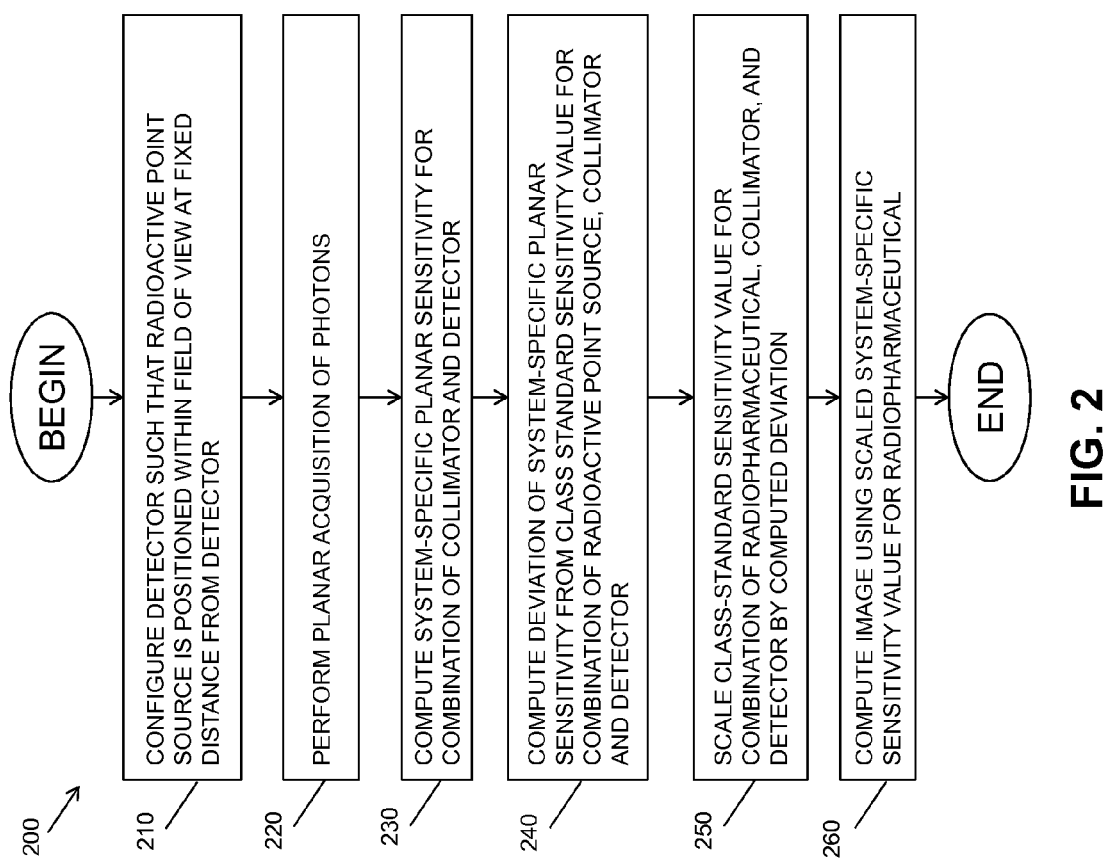
FIG. 2 is a flow diagram of a process of normalizing the sensitivity of a gamma camera in accordance with some embodiments.

FIG. 2 is a flow diagram of a process 200 of normalizing the sensitivity of a gamma camera in accordance with some embodiments. Sensitivity, which refers to the ability of a gamma camera to detect the activity of a radioactive sample, is the ratio of observed counts to number of disintegrations in the radioactive source. Sensitivity is expressed in units of counts/sec/MBq (also referred to as cps/MBq), where 1 Bq (or becquerel) corresponds to one decay per second. In non-SI units, sensitivity may be expressed as counts/minute/μCi, where 1 Ci=$3.7 \times 10^{10}$ decays per second. At block 210, detector 130 is configured such that a calibration point source is positioned within a field of view (FOV) of the detector at a fixed distance from the detector. The calibration point source 112 may be positioned near the center of the FOV.

Block 220 includes performing a planar acquisition of gamma photons emitted by the calibration point source 112 and passed through collimator 120 (e.g., passed through respective holes of the collimator), until a predetermined number, e.g. 5 million counts of gamma photons have been acquired, e.g., in photopeak energy analyzer 135 which selects a fixed fraction of gamma ray photons that have undergone photoelectric conversion in the detector. The photoelectric effect results in a peak (photopeak), and a predetermined band around the photopeak is used for selecting photons.

At block 230, the system-specific planar sensitivity of the collimator-detector system (i.e., for collimator 120 and detector 130) is computed (e.g., by a processor of computer 160) using the number of gamma photons acquired, the time duration of the acquisition, and data regarding a precisely known, precalibrated (factory calibrated) amount of radioactive isotope (calibration point source 112). For example, a typical sensitivity calibration workflow includes acquiring 5 million counts in the photopeak analyzer window for each detector using the calibration point source 112 and computing the system specific sensitivity using the acquisition time, the number of acquired counts (5 million in this example) and the factory calibrated radioactivity data corrected for decay. The correction for decay may involve determining the duration of time that elapsed between the precalibration time (i.e., the time at which the factory calibration took place) and the acquisition time (the time at which the 5 million counts were acquired, in this example).

At block 240, the deviation of the computed system-specific planar sensitivity from a class standard sensitivity value for the combination of calibration point source 112, collimator 120, and detector 130 is computed (e.g., by a processor of computer 160). Class standard sensitivity values are available for various classes of medical imaging devices. The deviation from the class standard sensitivity value may be computed as a ratio. As an example, the class-standard sensitivity value for gamma ray photons from Co-57 using a Siemens Autoform LEHR collimator mounted on a ⅜ inch Foresight detector is 97 cps/MBq. If the sensitivity for a specific system turns out to be 95 cps/MBq then the deviation (e.g., expressed as a ratio) reported would be 95/97 or 0.979.

At block 250, a class standard sensitivity value for a combination of a radiopharmaceutical (e.g., a radiopharmaceutical administered to a patient in a clinical setting), the collimator 120, and the detector 130 is scaled by the computed deviation. This scaling yields a scaled system-specific sensitivity value for the radiopharmaceutical. As an example, for gamma ray photons from Tc-99m the class standard planar sensitivity for the Siemens Autoform LEHR collimator mounted on a ⅜ inch Foresight detector is 91 cps/MBq. If for a system in the field during the sensitivity calibration the Co-57 sensitivity was found to be 2.1% lower than its class standard value as in the example above, then the Tc-99m system specific sensitivity would be lowered 2.1% from 91 to 89.1 cps/MBq.

Figure 3:
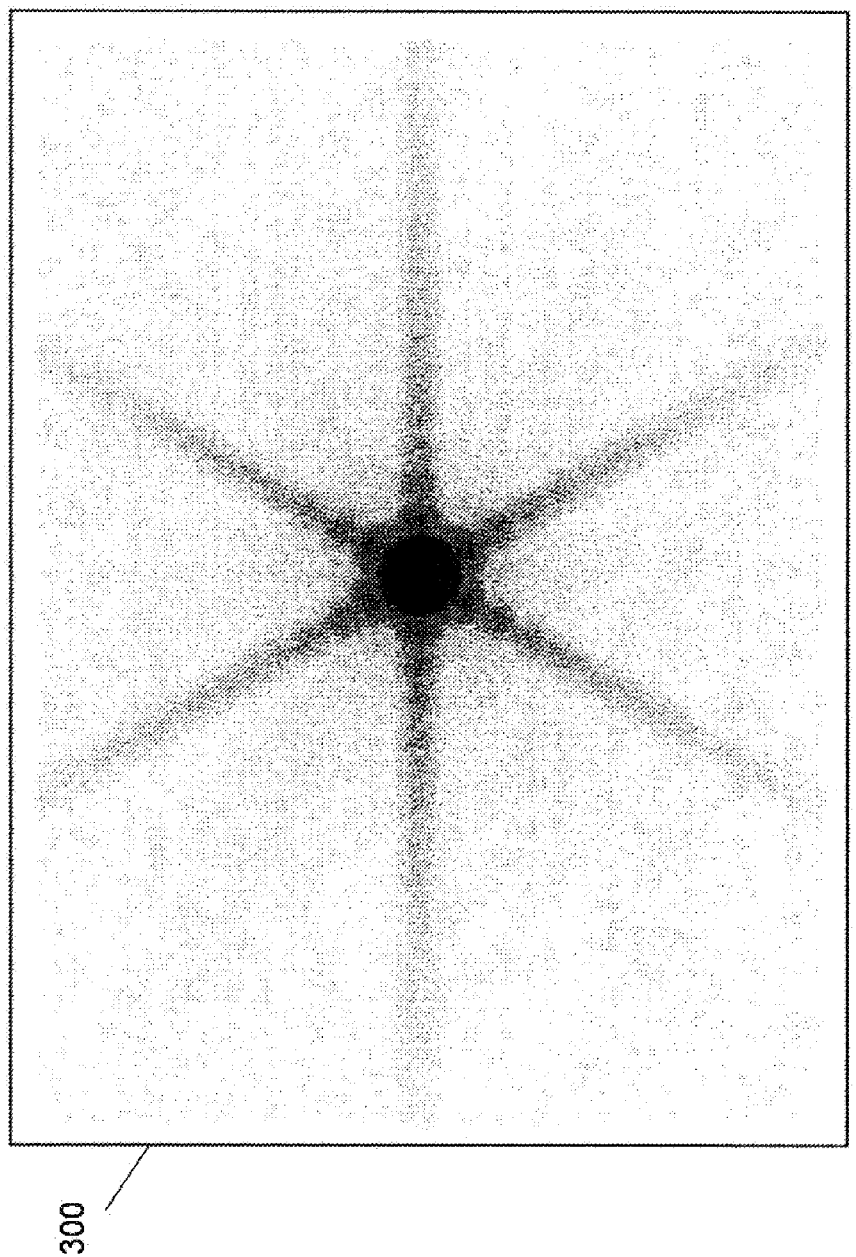
FIG. 3 shows a planar projection image for the photons in the photopeak window using a Tc-99m point source.

The scaled system-specific sensitivity value for the radiopharmaceutical may be used to compute an image (e.g., 3D SPECT image) at block 260. The image may be computed further based on a class standard value for a point source response function (PSRF) measured for a combination of the radiopharmaceutical, the collimator 120, the detector 130, and an imaging distance between the detector and an object plane. An example of a measured PSRF is shown in FIG. 3. The class standard PSRF is computed by averaging the measured PSRFs for a class of devices comprising a detector and a collimator, for a given radioisotope (in a radiopharmaceutical), and for a range of imaging distances (distance between the imaging plane within the detector and an object plane). The imaging plane is a virtual plane inside the detector where 95% of the incident gamma ray photons have undergone photoelectric conversion and as the object plane is an arbitrarily chosen plane in the object volume along the sagittal or coronal direction. The computed image has a plurality of values associated with respective pixels or voxels. It should be understood that the computed image does not have to be displayed, although it may be displayed.

In SPECT imaging projection data are generated by scanning a patient who has been injected with a radiopharmaceutical and the imaged object can be considered as a collection of point sources with each point corresponding to the size of an image voxel. Each voxel value of the computed SPECT image is indicative of an absolute rate of decay of the radiopharmaceutical per unit volume. Thus, through a normalization procedure involving scaling a standard sensitivity value by a computed deviation, absolute quantitative data are provided in the SPECT image, which has not been possible previously. The absolute quantitative data of such a quantitative SPECT image may be displayed visually, e.g., along with a legend on a display of computer 160 for viewing by a human, or may be processed automatically in other algorithm(s) such as automatic classification or diagnosis routines.

Additional details regarding gamma photon acquisition and intuition underlying the above-described normalization process are now provided. For SPECT imaging, emitted photons from respective point sources, attenuated by an object (e.g., part of the body of a patient), are detected by the gamma camera with a spatial distribution that is given by the distance-dependent point source response function (PSRF), and the number of photons detected by the camera per unit time per unit of activity is the system point source planar sensitivity. Each pixel in the projection data represents the line integral of the photons along a line-of-sight (LOS), attenuated by the object, and convolved by the distance dependent PSRF. An additional blurring of the image formation occurs by photons that are not emitted by voxels along this line-of-sight, but are scattered into the line-of-sight by the object, and this blurring may be compensated by the reconstruction engine via a scatter correction procedure.

The image formation process for SPECT can be mathematically summarized as:

$$m_i = \Sigma H_{i\alpha} I_\alpha + s_i \quad (1)$$

for all i, where the summation is performed over $\alpha$, where $m_i$ are the counts in the $i^{th}$ pixel in the projection data, $I_\alpha$ is the activity concentration in voxel $\alpha$, H is the system matrix that represents the entire image formation process, and $s_i$ is the scatter estimate.

For SPECT imaging using multi-channel collimators, the PSRF is not only determined by the channel geometry (hole shape and size) but also by the collimator material properties. Gamma-ray interaction with matter results in intensity attenuation that follows an exponential law as follows:

$$I = I_0 e^{-\mu x} \quad (2)$$

where $\mu$ is the linear attenuation coefficient that is a function of the gamma ray energy and the material property, and x is the areal density (thickness) of the material.

The equation (2) above for intensity attenuation implies that the intensity of the gamma rays will be reduced to zero for an infinitely thick slab of material. As a result, some of the gamma rays incident on collimator 120 will penetrate through the septa, and the resulting PSRF has a septal penetration pattern that spans the entire field of view of detector 130 as shown in FIG. 2.

FIG. 3 shows a planar projection image 300 for the photons in the photopeak window using a Tc-99m point source. The spatial distribution of counts is shown in image 300. The number of counts per unit time and activity is the system sensitivity or photopeak detection efficiency of the system. The system sensitivity is specific to a system and corresponds to a narrow tolerance band, e.g., ±1.5% for a Siemens Autoform LEHR collimator mounted on a freshly calibrated ⅜ inch Foresight detector, around a class standard due to manufacturing tolerances. The Tc-99m source needs to be calibrated using a dose calibrator that can introduce uncertainties in the calibration process. Therefore, it is desirable to calibrate the system sensitivity of each system using a factory calibrated source with traceable activity calibration to remove the system variability and provide a common baseline for all systems in the field. Such a calibration source may have the following attributes:

1) The radioisotope used for calibration should have a reasonably long (e.g. >6 months) half-life so that the source does not need to be replaced too frequently which would add cost and logistical complexity to the clinical workflow. In addition, the handling of such a source should take into consideration issues related to human health and safety. For this reason, the radioisotope may be encapsulated in a metallic container (e.g., metallic enclosure 112 shown in FIG. 1).

2) The calibration radioisotope should emit a gamma ray with energy that is close to (e.g., ±10% of) the energy of the gamma ray from a clinical radioisotope (i.e., a radioisotope used in a clinical setting for imaging a patient).

3) Gamma ray yield per disintegration from the calibration radioisotope should be large enough such that the calibration does not take an inordinately long time (e.g., so that calibration can be completed in 30 minutes or less).

4) The fraction of gamma-rays that are scattered in the source should be reasonably small (e.g., <10%) so that the calibration process does not take too long (calibration can be completed in 30 minutes or less) to achieve statistical accuracy. The source configuration should be such that the Compton scattering events are either rejected by the collimator acceptance angle or by detector energy discrimination.

A radioactive source comprising cobalt-57 (57Co or Co-57) achieves all of the requirements above and may be used for system sensitivity calibration. Other radioisotopes that may be used for calibration include Cd-109, Gd-153, Ba-133, Sn-113, Ce-139, Eu-152, Rh-101, Lu-176, Hf-182. Calibration using a 57Co source in accordance with some embodiments provides the foundation for obtaining quantitative SPECT images using clinical radiotracers (e.g., Tc-99m labeled radiotracers) that are free of system-specific variations.

Figure 4:
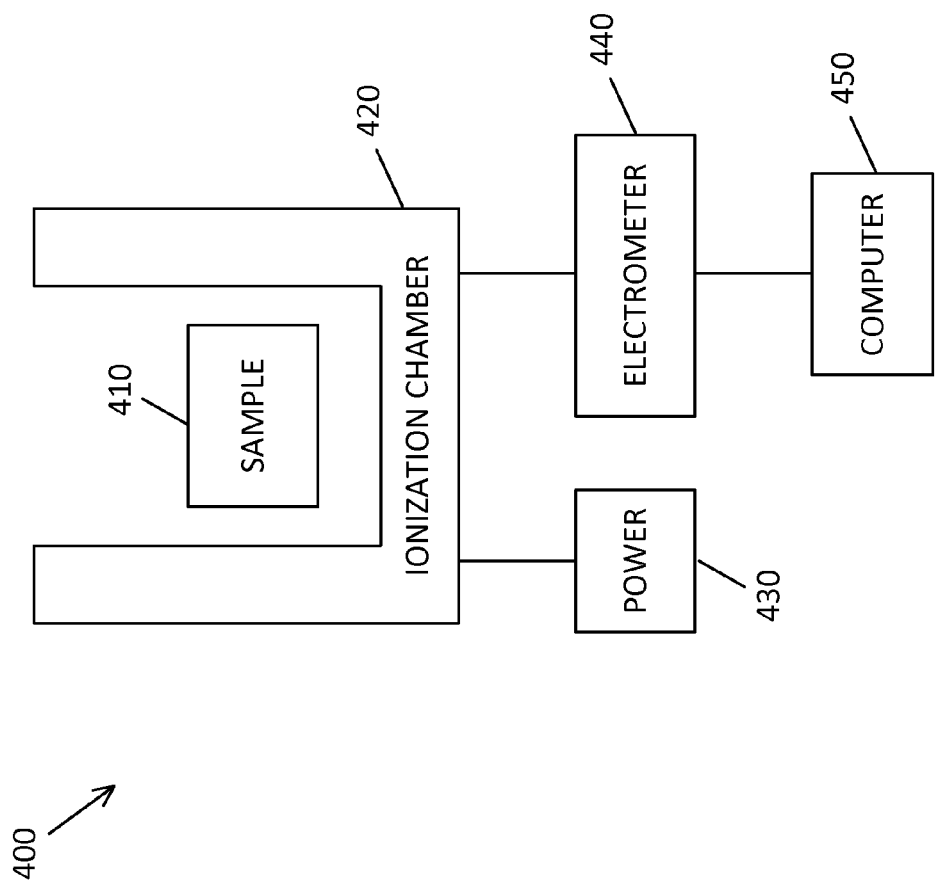
FIG. 4 is a diagram of a dose calibrator.

A dose calibrator is typically used to calibrate the amount of radioactivity administered to a patient, e.g., for assaying radiopharmaceuticals. A typical dose calibrator 400 (also known as radionuclide calibrator or radionuclide dose calibrator) is depicted in FIG. 4. An ionization chamber 420 (ion chamber) containing a gas (e.g., argon) and a pair of electrodes is used for measuring the ionization produced by a radioactive sample 410. A power supply 430 provides a high voltage that causes ions produced by ionization of the gas ionization to collect at the electrodes. An ionization current is produced which has a magnitude proportional to the activity of the sample 410. An electrometer 440 measures the ionization current. The output of the electrometer may be processed by a computer 450, which may provide an output reading that is displayed to an operator. Dose calibrators are described further in "The Selection, Use, Calibration, and Quality Assurance of Radionuclide Calibrators Used in Nuclear Medicine," Report of AAPM Task Group 181, ISBN 978-1-936366-18-7, the entire contents of which are hereby incorporated by reference herein. Dose calibrators can fall out of calibration, which can be deleterious to the health of patients who are administered radiopharmaceuticals. Therefore, in some embodiments of the present disclosure, identification of a miscalibrated dose calibrator improves the efficiency and safety of administered radiopharmaceuticals.

Figure 5:
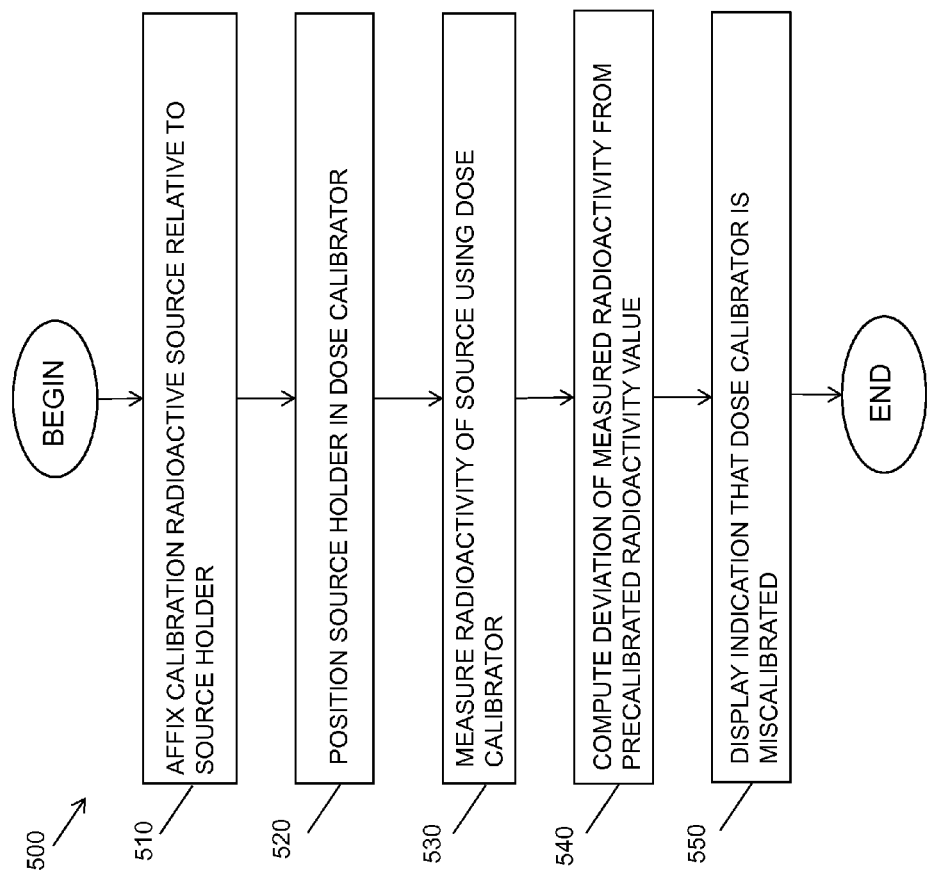
FIG. 5 is a flow diagram of a process for identifying a miscalibrated dose calibrator in accordance with some embodiments.
Figure 6:
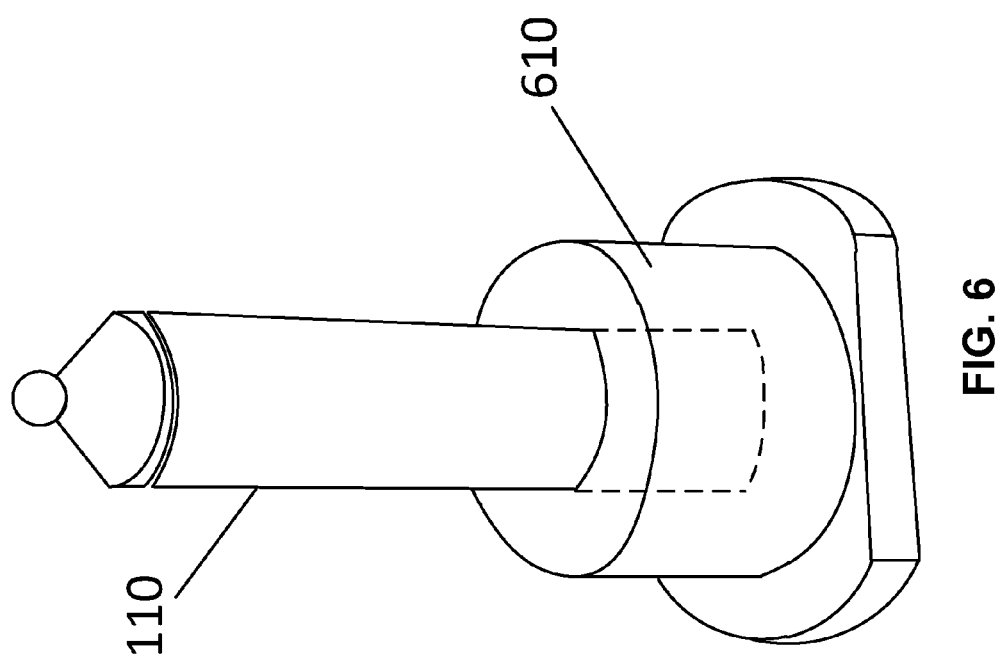
FIG. 6 is a diagram of a radioactive source positioned within a source holder.

FIG. 5 is a flow diagram of a process 500 for identifying a miscalibrated dose calibrator. At block 510, a calibration radioactive source is affixed relative to a source holder. For example, the source (e.g., source 110) may be positioned within an acrylic source holder 610 shown in FIG. 6. At block 520, the source holder is positioned in a dose calibrator (e.g., within a container that is placed in the ionization chamber 420 of dose calibrator 400). As a result, the source is placed in the dose calibrator in a repeatable configuration, e.g., at a region of optimum sensitivity. At block 530, a radioactivity measurement generated by the dose calibrator is obtained. A deviation of the measured activity from a factory-calibrated radioactivity value is computed (block 540), e.g., by a processor of a computer such as computer 450. If the computed deviation is less than (or greater than, depending on the implementation) a predetermined threshold, an indication is provided (e.g., at a display of computer 450) to indicate that the dose calibrator is out of calibration (miscalibrated).

The ability to identify a miscalibrated dose calibrator is an important feature because even if the quantitatively reconstructed image (e.g., activity concentration in units of Bq/voxel or Bq/ml) is accurate, in clinical practice the measure often used for metabolic uptake is a Standardized Uptake Value (SUV), which is the activity concentration divided by the injected dose and the patient weight. Therefore, any uncertainty in the injected activity that is dose calibrated in the clinical setting (e.g., hospital) directly feeds into the SUV computation.

Figure 7:
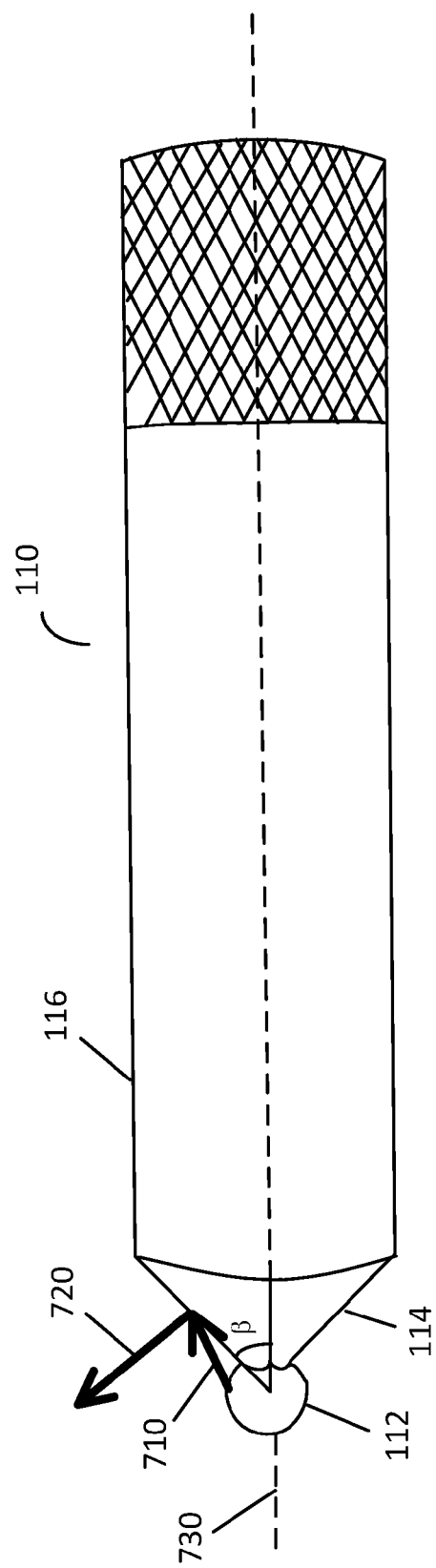
FIG. 7 is an illustration of a calibration source in accordance with some embodiments.

FIG. 7 is an illustration of calibration source 110. Enclosure 112, transition portion 114, and handle portion 116 are aligned along an axis 730. Transition portion 114 may be substantially conical. The scatterer response of calibration source 110 is substantially the same, within a statistical error bound (e.g., ±1%) as for a true point source that would be present with an injected radiotracer. This scattering response of the calibration source 110 is achieved because the bevel angle β defined between axis 730 and the surface of transition portion 114 is selected such that photons directly impinging upon the detector 130 after passing through the collimator 120 are only minimally impeded. In some embodiments, a bevel angle β in the range of about 47 to 51 degrees is effective for achieving this minimization of the number of Compton-scattered gamma photons emitted by the radioactive isotope that are collimated and detected. In contrast, photons scattered by the holder (see arrows 710 and 720 for such a photon trajectory) are either rejected by the collimator acceptance angle (e.g., about 3°) or are rejected by the lower bound of the energy analyzer scatter window, which for 57Co is at about 113 keV for a 15% window width centered on the Co-57 photopeak energy of 122 keV.

The optimal bevel angle β for the 57Co radioactive source is about 49°. This optimal angle is a function of the incident photon energy and the detector energy analyzer setting and is physics-based. The ratio of Compton scattered photons to photopeak photons is very close to that for a true point source, and the attenuation of photons due to the metallic enclosure 112 around the active element (radioisotope) is approximately uniform for typical analyzer settings. Thus, problems typically associated with the anisotropic nature of photon emissions from typical sealed sources are overcome in embodiments of the present disclosure.

Figure 8:
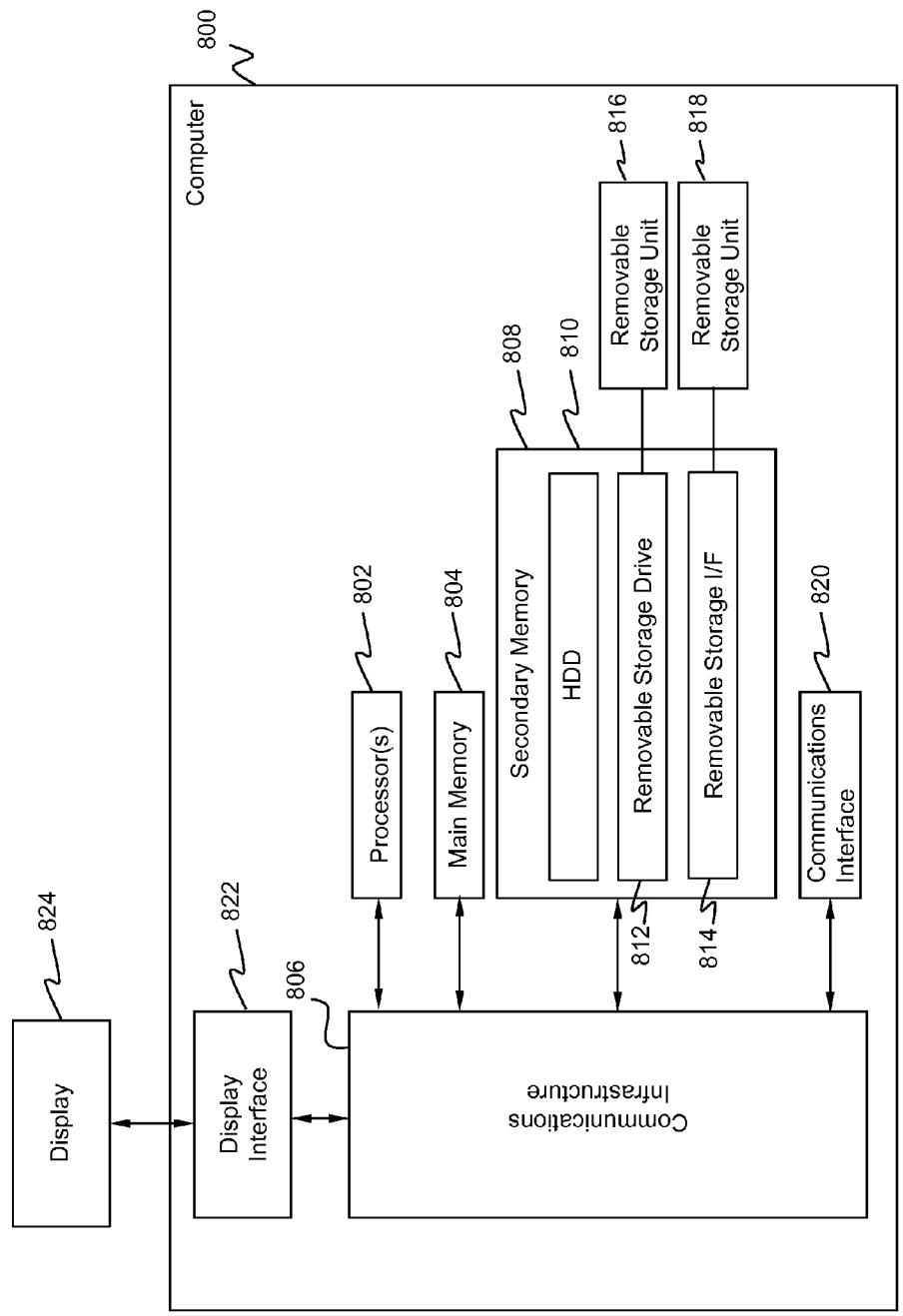
FIG. 8 is an architecture diagram of a computer system that may be used in some embodiments.

FIG. 8 is an architecture diagram of a computer system 800 that may be used in some embodiments. Computer system may be used to implement computer 160 or computer 450. Computer system 800 may include one or more processors 802. Each processor 802 is connected to a communication infrastructure 806 (e.g., a communications bus, cross-over bar, or network). Computer system 800 may include a display interface 822 that forwards graphics, text, and other data from the communication infrastructure 806 (or from a frame buffer, not shown) for display on the display unit 824.

Computer system 800 may also include a main memory 804, such as a random access memory (RAM), and a secondary memory 808. The secondary memory 808 may include, for example, a hard disk drive (HDD) 810 and/or removable storage drive 812, which may represent a floppy disk drive, a magnetic tape drive, an optical disk drive, a memory stick, or the like as is known in the art. The removable storage drive 812 reads from and/or writes to a removable storage unit 816. Removable storage unit 816 may be a floppy disk, magnetic tape, optical disk, or the like. As will be understood, the removable storage unit 816 may include a computer readable storage medium having tangibly stored therein (embodied thereon) data and/or computer software instructions, e.g., for causing the processor(s) to perform various operations.

In alternative embodiments, secondary memory 808 may include other similar devices for allowing computer programs or other instructions to be loaded into computer system 800. Secondary memory 808 may include a removable storage unit 818 and a corresponding removable storage interface 814, which may be similar to removable storage drive 812, with its own removable storage unit 816. Examples of such removable storage units include, but are not limited to, USB or flash drives, which allow software and data to be transferred from the removable storage unit 816, 818 to computer system 800.

Computer system 800 may also include a communications interface 820. Communications interface 820 allows software and data to be transferred between computer system 800 and external devices. Examples of communications interface 820 may include a modem, Ethernet card, wireless network card, a Personal Computer Memory Card International Association (PCMCIA) slot and card, or the like. Software and data transferred via communications interface 820 may be in the form of signals, which may be electronic, electromagnetic, optical, or the like that are capable of being received by communications interface 820. These signals may be provided to communications interface 820 via a communications path (e.g., channel), which may be implemented using wire, cable, fiber optics, a telephone line, a cellular link, a radio frequency (RF) link and other communication channels.

In this document, the terms "computer program medium" and "non-transitory computer-readable storage medium" refer to media such as, but not limited to, media at removable storage drive 812, or a hard disk installed in hard disk drive 810, or removable storage unit 816. These computer program products provide software to computer system 800. Computer programs (also referred to as computer control logic) may be stored in main memory 804 and/or secondary memory 808. Computer programs may also be received via communications interface 820. Such computer programs, when executed by a processor, enable the computer system 800 to perform the features of the methods discussed herein. For example, main memory 804, secondary memory 808, or removable storage units 816 or 818 may be encoded with computer program code (instructions) for performing operations corresponding to various processes disclosed herein.

It is understood by those familiar with the art that the system described herein may be implemented in hardware, firmware, or software encoded (e.g., as instructions executable by a processor) on a non-transitory computer-readable storage medium.

The systems and processes are not limited to the specific embodiments described herein. In addition, components of each system and each process can be practiced independent and separate from other components and processes described herein.

The previous description of the embodiments is provided to enable any person skilled in the art to practice the disclosure. The various modifications to these embodiments will be readily apparent to those skilled in the art, and the generic principles defined herein may be applied to other embodiments without the use of inventive faculty. The present disclosure is not intended to be limited to the embodiments shown herein, but is to be accorded the widest scope consistent with the principles and novel features disclosed herein.

What is claimed is:

1. A method of normalizing a sensitivity of a gamma camera, the method comprising:
    configuring a detector of a gamma camera such that a radioactive point source is positioned within a field of view of the detector at a fixed distance from the detector;
    performing a planar acquisition of gamma photons emitted by the radioactive point source and passed through a collimator, until a predetermined number of photons have been acquired;
    computing a system-specific planar sensitivity for a combination of the collimator and detector using the number of gamma photons acquired, a time duration of the acquisition, and precalibrated radioactivity data of the radioactive point source corrected for decay that occurred after a precalibration time;
    computing a deviation of the computed system-specific planar sensitivity from a class standard sensitivity value for a combination of the radioactive point source, the collimator, and the detector; and
    scaling a class standard sensitivity value for a combination of a radiopharmaceutical, the collimator, and the detector by the computed deviation, to yield a scaled system-specific sensitivity value for the radiopharmaceutical.

2. The method of claim 1, further comprising generating an image using the radiopharmaceutical, the collimator, and the detector, wherein the image is computed using at least the scaled system-specific sensitivity value for the radiopharmaceutical.

3. The method of claim 2, wherein the image is a 3D single photon emission computed tomography (SPECT) image including a plurality of voxels, and each voxel value of the image is indicative of an absolute rate of decay of the radiopharmaceutical per unit volume.

4. The method of claim 3, further comprising displaying the 3D SPECT image with a legend indicating absolute quantitative information about the voxel values.

5. The method of claim 3, further comprising providing at least a subset of the voxel values of the 3D SPECT image as input to an automatic classifier.

6. The method of claim 2, wherein the image is computed further using a class standard value for a point source response function measured for a combination of the radiopharmaceutical, the collimator, the detector, and an imaging distance between the detector and an object plane.

7. The method of claim 1, wherein the planar acquisition is performed until the predetermined number of photons have been acquired at a photopeak energy analyzer of the gamma camera for a predetermined band around a photopeak.

8. The method of claim 1, wherein the radioactive point source is selected from the group consisting of Co-57, Cd-109, Gd-153, Ba-133, Sn-113, Ce-139, Eu-152, Rh-101, Lu-176, and Hf-182.

9. The method of claim 8, wherein the radioactive point source is Co-57.

10. A device comprising:
    a radioactive point source;
    a collimator;
    a gamma ray detector configured to detect gamma photons emitted by the radioactive point source and passed through the collimator;
    one or more computer processors; and
    a non-transitory computer readable medium having instructions embodied tangibly thereupon, the instructions when executed configured to cause the one or more processors to perform operations of normalizing a sensitivity of a gamma camera, the operations comprising:
computing a system-specific planar sensitivity for a combination of the collimator and detector using a number of gamma photons acquired, a time duration of acquisition of the number of gamma photons, and precalibrated radioactivity data of the radioactive point source corrected for decay that occurred after a precalibration time;
computing a deviation of the computed system-specific planar sensitivity from a class standard sensitivity value for a combination of the radioactive point source, the collimator, and the detector; and
scaling a class standard sensitivity value for a combination of a radiopharmaceutical, the collimator, and the detector by the computed deviation, to yield a scaled system-specific sensitivity value for the radiopharmaceutical.

11. The device of claim 10, wherein the operations further comprise generating an image using the radiopharmaceutical, the collimator, and the detector, wherein the image is computed using at least the scaled system-specific sensitivity value for the radiopharmaceutical.

12. The device of claim 11, wherein the image is a 3D single photon emission computed tomography (SPECT) image including a plurality of voxels, and each voxel value of the image is indicative of an absolute rate of decay of the radiopharmaceutical per unit volume.

13. The device of claim 12, wherein the operations further comprise displaying the 3D SPECT image with a legend indicating absolute quantitative information about the voxel values.

14. The device of claim 10, wherein the radioactive point source is selected from the group consisting of Co-57, Cd-109, Gd-153, Ba-133, Sn-113, Ce-139, Eu-152, Rh-101, Lu-176, and Hf-182.

15. The device of claim 14, wherein the radioactive point source is Co-57.

* * * * *